United States Patent [19]
Nakayama et al.

[11] Patent Number: 5,270,190
[45] Date of Patent: Dec. 14, 1993

[54] METHOD FOR PRODUCING (R)-MALIC ACID FROM MALEIC ACID USING MICROBIAL MALEATE HYDRATASE

[75] Inventors: Kiyoshi Nakayama; Yukie Kobayashi, both of Kanagawa, Japan

[73] Assignee: Bior Inc., Tokyo, Japan

[21] Appl. No.: 821,197

[22] Filed: Jan. 15, 1992

[51] Int. Cl.$^5$ .............................. C12P 7/46; C12N 9/88
[52] U.S. Cl. ..................................... 435/145; 435/232; 435/822; 435/911
[58] Field of Search ............... 435/145, 232, 280, 822, 435/911

[56] References Cited
FOREIGN PATENT DOCUMENTS 56-42589  4/1981  Japan .

OTHER PUBLICATIONS
Hopper D. J. et al, Biochem J. 110:798–800 (1968).
Rahatekar Hi, Indian J. Biochem 5:143–4 (1968).

*Primary Examiner*—Douglas W. Robinson
*Assistant Examiner*—S. Saucier
*Attorney, Agent, or Firm*—Sughrue, Mion, Zinn, Macpeak & Seas

[57] ABSTRACT

This invention relates to a method for producing (R)-malic acid comprising contacting, in a reaction medium, maleic acid with (A) a microbial maleate hydratase capable of hydrating maleic acid to form (R)-malic acid or (B) a microorganism containing the maleate hydratase, microbial maleate hydratase and a method for producing same. In accordance with the present invention (R)-malic acid with high optical purity is supplied efficiently and economically.

5 Claims, No Drawings

METHOD FOR PRODUCING (R)-MALIC ACID FROM MALEIC ACID USING MICROBIAL MALEATE HYDRATASE

This is a continuation-in-part application of International Application Ser. No PCT/JP91/00025 filed Jan. 14, 1991.

FIELD OF THE INVENTION

The present invention relates to a method for producing (R)-malic acid [D-(+)-malic acid] by hydrating maleic acid. The present invention also relates to an enzyme catalyzing a reaction in which maleic acid is hydrated into (R)-malic acid and a method for producing the enzyme.

BACKGROUND OF THE INVENTION (R)-malic acid [D-(+)-malic acid] is an unnatural malic acid and is useful as a precursor for the synthesis of various chiral compounds such as an optically active isoserine, an optically active pantolactone, an optically active β-lactam intermediates and an optically active pheromones.

Although L-(−)-malic aid occurs naturally and now being produced from fumaric acid by enzymic method, no efficient process for (R)-malic acid production was developed until now. Chemical hydration of fumaric acid or maleic acid anhydride produce DL-malic acid (racemic malic acid). Several syntheses of (R)-malic acid or its derivatives have been known. Wynberg, Staring et al. [Wynberg, H., Staring, E. G. J., *J. Amer. Chem. Soc.*, Vol. 104, pp. 166 to 168 (1982)] synthesized (R)-malic acid in 79% overall yield by application of asymmetric cycloaddition catalyzed by quinidine. Henrot et al. [Henrot, S., Larcheveque, M., Petit, Y., *J. Chem. Soc., Perkin Trans.* 1. *Synth. Commun.*, Vol. 16, p. 183 (1986)]described the synthesis of (R)-malic acid from (R)-aspartic acid in three steps and 68% overall yield. Seebach et al. [Hungerbühler, E., Seebach, D., Wasmuth, D., *Helv. Chim. Acta.*, Vol. 64, p. 1467 (1981)] and also Alpegiani et al. [Alpegiani, M. and Hanessian, S., *J. Org. Chem.*, Vol. 52, pp. 278 to 279 (1987)] described the synthesis of (R)-dimethyl malate from (R,R)-dimethyl tartarate.

(R)-malic acid was also prepared by resolution of DL-malic acid as described in German Patent Application (OLS) No. 2,933,895, JP-A-57-56439, JP-A-60-204741 (the term "JP-A" as used herein refers to a "published unexamined Japanese patent application"), EP-A-149,885 (the term "EP-A" as used herein refers to a "published unexamined European patent application"), *Synthesis*, p. 214 (1985), and U.S. Pat. No. 4,912,042. High performance liquid chromatography resolved DL-malic acid [Benecke, I , *J. Chromatogr.*, Vol. 291, p. 155 (1984)]. Rom 67,279 (1979) [*Chem. Abstr.*, Vol. 93, 238846a (1980)] described asymmetric synthesis using polarized electrets.

However, these methods are disadvantageous from an industrial viewpoint since the starting materials or resolving agents are expensive. The formation of (S)-malic acid by enzymic method is known as described in Kitahara, K., Fukui, S. and Misawa, M., *J. Gen. Appl. Microbiol.*, Vol. 6, p. 108 (1960). (S)-malic acid was also produced from maleic acid via fumaric acid by a bacterium which has cis-trans-isomerase catalyzing the formation of fumaric acid from maleate [Otsuka, K., *Agric. Biol. Chem.*, Vol. 25, p. 726 (1961)]. Sacks, W. and Jensen, C. O. [Sacks, W., Jensen, C. O., *J. Biol. Chem.*, Vol. 192, p. 231 (1951)] obtained malic acid from maleic acid using a hydratase from corn kernels but enantiomorph of the malic acid formed was not specified. D-malate formation from maleic acid was noted with the extract of mammalian kidney [Taggart, J. V., Angielski, S., Morell, H., *Biochem. Biophys. Acta.*, Vol. 185, p. 220 (1969)]. (R)-malic acid formation from maleic acid using cell-extract of a Pseudomonas strain isolated from soil is described in Rahatekar, H. L., Maskatl, F. S., Subramanian, S. S., Raghavendra Rao, M. R., *Indian J. Biochem.*, Vol. 5, p. 143 (1968) and Hopper, D. J., Chapman, P. J., Sagney, S., *Biochem. J.*, Vol. 110, p. 798 (1968). However, the properties of the enzyme has never been specified and no industrial method enabling the supply of (R)-malic acid has never been developed.

SUMMARY OF THE INVENTION

An object of the present invention is to overcome the above-described disadvantage of the prior art and provide a method for producing (R)-malic acid biochemically and efficiently.

Another object of the present invention is to provide a novel enzyme useful in the biochemical production of (R)-malic acid and a method for efficiently producing the enzyme.

In view of the usefulness of (R)-malic acid, intensive investigation has been made on a biochemical method for producing (R)-malic acid from maleic acid available inexpensively. Not only microorganisms from culture collection have been investigated but also newly isolated microorganisms have been investigated for an appropriate enzyme. As a result, a novel enzyme, microbial maleate hydratase, has been found in the present invention to be useful in the biochemical hydration of maleic acid to obtain (R)-malic acid and a method for producing this enzyme efficiently has been also found in the present invention.

Therefore, in one embodiment, the present invention provides a method for producing (R)-malic acid comprising hydrating maleic acid by contacting, in a reaction medium, maleic acid with (A) a microbial maleate hydratase capable of hydrating maleic acid to form (R)-malic acid or (B) a microorganism containing the maleate hydratase. In another embodiment, the present invention provides a method for producing microbial maleate hydratase by cultivating microorganism capable of producing the maleate hydratase in the presence of a certain organic substance.

DETAILED DESCRIPTION OF THE INVENTION

The microorganisms which can be used in the present invention contain maleate hydratase which hydrates maleic acid to form (R)-malic acid. The enzyme used in the method of the present invention is an enzyme capable of hydrating maleic acid to produce (R)-malic acid and is named maleate hydratase. The enzyme is classified as class 4.2.1.31 according to the nomenclature of the international enzyme classification.

Microorganisms which produce an enzyme capable of converting maleic acid into (R)-malic acid can be selectively isolated based on the capability of producing (R)-malic acid from maleic acid and distributed ubiquitously in microorganisms including bacteria, fungi and yeast. Examples of such microorganisms include bacteria belonging to the genera, Arthrobacter, Brevibacterium, Corynebacterium, Bacillus, Acinetobacter, Pseudomonas, Microbacterium, Aeromonas, Escherichia, Alcaligenes, Proteus, Providencia, Paracoccus, Protaminobacter, Serratia, Xanthomonas, Amycoplatopsis, Streptomyces, Rhodococcus, Cellulomonas, Hafnia, Cytophaga, Flavobacterium, Klebsiella, Micrococcus, Ancylobacter, Morganella, Planococcus, Kluyvera, Kurthia, Achromobacter, and Citrobacter. Examples of the yeast to be used include Saccharomyces, Saccharomycopsis, Yarrowia, Candida, Debaryomyces, Hansenula, Kloeckera, Kluyveromyces, Lipomyces, Rhodotorula, Schizosaccharomyces, Torulopsis, Trichosporon, and Trigonopsis. Examples of the fungi to be used include the microorganisms of the genera, Aspergillus, Penicillium, Rhizopus, and Trichoderma. Particular examples of the microbial strains to be used are those shown in examples. These microbial strains are available from type culture collections (ATCC: American Type Culture Collection, Rockville, Md., U.S.A., IFO: Institute For Fermentation, Osaka, Japan). These microorganisms can be wild strain or mutants. Strains containing genes for maleate hydratase obtainable by DNA recombination technique can also be used in the present invention.

The microbial maleate hydratase can be those extracted from the above described microorganisms cells or the cultured broth. Immobilized enzymes and immobilized microorganisms containing the enzymes can also be employed as long as they exhibit maleate hydratase activity.

In order to obtain a culture containing a maleate hydratase activity by cultivating microorganism capable of producing this enzyme, usual cultivation methods can be used; namely cultivating in a nutrient medium containing organic compounds as a carbon source, organic and/or inorganic compounds as a nitrogen source, and mineral salts, at pH 4 to 10, at 10° to 40° C. It is preferred to add at least one compound selected from the group consisting of maleic acid and citraconic acid since a culture having high maleate hydratase activity can be obtained by the addition of such compound. The concentration of these compounds to be added in a medium is generally from about 0.1 to 3% by weight, preferably from about 0.5 to 2% by weight. The effect of these compounds is shown in Table 1 hereinbelow and Examples 1 and 2. From these data, it can be seen that the medium containing at least one such compound increases the yield of the enzyme remarkably.

TABLE 1

Induction of maleate hydratase by citraconic acid and maleic acid in *Brevibacterium helvolum* ATCC 11822

| Addition to Basal Medium* | Growth at 68 Hours O.D. (660 nm) | Specific Activity** | Induction Fold |
|---|---|---|---|
| None | 1.5 | 0.65 | 1.0 |
| Citraconic Acid (1%) | 4.1 | 3.13 | 4.8 |
| Maleic Acid (1%) | 4.5 | 2.56 | 3.9 |

*Basal Medium: $NH_4Cl$ 0.1%, $KH_2PO_4$ 0.14%, $Na_2HPO_4 \cdot 12H_2O$ 0.31%, $MgSO_4 \cdot 7H_2O$ 0.025%, meat extract 5.0% (%: w/v).
**Determined by the amount of (R)-malic acid formed when reaction mixture (total volume 2,000 μl, pH 7.2) containing 50 mM Tris-HCl buffer (1,700 μl), 100 mM maleate (200 μl), and crude enzyme preparation (cells sonicate supernatant, 100 μl) was reacted at 30° C. for 60 minutes.

Furthermore, both solid medium and liquid medium can be used in the present invention. Other conditions of cultivation of the enzyme producing microorganisms can be selected appropriately such that the strains can grow well according to the knowledge of those skilled in the art.

Although upon prolonged cultivation or addition of a releasing agent the enzyme is usually released from the cells and is obtainable by centrifugation of the broth, the malate hydratase contained in the cells can be released as a crude enzyme solution by destructing the cells by grinding or ultrasonication and extracting the enzyme therefrom. Of course, the cells as they are can be used as an enzyme preparation.

Purified maleate hydratase can be obtained from the crude enzyme solution by conventional enzyme purification methods such as an organic solvent fractionation method, an ammonium sulfate differential precipitation method, dialysis, isoelectric point precipitation method, and column chromatography alone or in combination. When a solid medium is used, water is added to the solid medium containing microbial cells, and the mixture as it is or after collecting the cells is subjected to the above-described ultrasonication or the like treatment to obtain a crude enzyme solution.

Of course, the maleic acid as a substrate can be used in the form of a physiolgically acceptable salt thereof, e.g., sodium salt or potassium salt, and the resulting (R)-malic acid can be also obtained in the form of salt thereof, e.g., sodium salt or potassium salt.

The microorganism cells having maleate hydratase activity or enzyme preparation derived therefrom thus obtained can be contacted with the substrate by adding the enzyme preparation in a solution containing the substrate and incubating the reaction mixture until the reaction proceeds or by adding the substrate in a culture broth of the microorganism followed by incubation for reaction. Alternatively, the enzyme can be contacted with the substrate in the form of enzyme preparations or cells separated from a culture broth of the microorganism of the present invention, physicochemically or biochemically treated cells such as washed cells, lyophilized cells and acetone-dried cells, extract solution, purified preparations, immobilized preparations, etc.

The concentration of the substrate varies depending on whether a batch system or a continuous system is used. In the batch system, it ranges generally from about 0.1 to 30%, preferably from about 0.5 to 10% by weight based on the weight of the reaction medium. In the continuous system, slightly lower ranges of the concentration, namely 0.05 to 20% by weight, is preferred. The reaction can be carried out usually at about 5° to 50° C., preferably at about 20° to 45° C., at a pH of about 4 to 10, preferably at a pH of about 6 to 9. The reaction time varies depending on the means of standing, stirring, flowing down through the column containing the immobilized enzyme, etc., or the form or activity of the enzyme but usually it ranges from about 1 to 100 hours.

The process of the reaction can be monitored by monitoring the generation of malic acid using, thin layer chromatography or high performance liquid chromatography. The malate concentration in a reaction mixture can be determined also by colorimetrically after reaction with the mixture of sulfuric acid and 2,7-naphthalenediol according to the method of Goodban, A. E. and Stark, J. B., *Anal. Chem.*, Vol. 29, p. 283 (1957). (R)-malic acid in the reaction mixture is monitored by the method of Krebs, H. A. and Egglestone, L. V., *Biochem. J.*, Vol. 37, p. 334 (1943)] Based on these values (malic acid and (R)-malic acid), optical purity of the (R)-malic acid in the reaction mixture can be estimated.

The value of the optical purity is not exactly correct but the method is conveniently applicable for tracing the reaction. Exact optical purity of the reaction mixture and isolated (R)-malic acid is determined by high performance liquid chromatography which enables the resolution of DL-malic acid into (R)-malic acid and (S)-malic acid. The conditions of the chromatography are as follows: column, MCI GEL CRS 10W (4.6×50 mm) (made by Mitsubishi Kasei, Japan); eluent, 0.5 mM $CuSO_4$/10% (v/v) acetonitrile; velocity, 1.3 ml/min.; temperature, 25° to 26° C.; detection, at 258 nm. Specific rotation of the product is also determined for the determination of the optical purity of the isolated product.

Hereinafter, the enzymological characteristics of microbial maleate hydratase of the present invention will be explained.

(1) Action and specificity

The enzyme catalyzes a reaction in which maleic acid is hydrated to form (R)-malic acid. It does not act on fumaric acid.

(2) Optimum pH

The enzyme is active at pH 6.0 to 9.0 and most active at 7.0 to 8.0.

(3) pH stability

The enzyme is stable generally at pH 6.0 to 9.0 and particularly at pH 7.0 to 8.0.

(4) Optimum temperature

The enzyme acts well at 20° to 50° C. and its optimum temperature is about 40° C.

(5) Temperature stability

The enzyme is stable below 35° C. At 45° C. or more it inactivates rapidly.

(6) Molecular weight

The molecular weight of the enzyme estimated by the gel filtration method (using Sepharose 4B) is about $13.5 \times 10^4$. Using Sephacryl S-200, the value is about $6 \times 10^4$.

(7) Inhibitors

In a concentration of 1 mM, PCMB (p-chloromercuribenzoic acid) inhibits 100% activity, but EDTA and PMSF (phenylmethylsulfonylfluoride) shows no inhibition. IAA (iodoacetic acid) and $NaIO_4$ (sodium metaperiodate) inhibits 12% and 17%, respectively. NEM (N-ethylmaleimide) shows 33% inhibition at 10 mM. Thus, the enzyme seems to contain SH group in its active site.

For the recovery of (R)-malic acid from the reaction mixture, known method for (S)-malic acid can be applied. Thus, ion-exchange treatment, concentration and crystallization process are applied after removal of solids such as cells from the reaction mixture by centrifugation or filtration.

Hereinafter, the present invention will be described in greater detail with reference to examples which should by no means construed as limiting the present invention thereto. In the following examples all percentages are by weight unless otherwise indicated.

EXAMPLE 1

A large test tube (2.4×19.5 mm) containing 5 ml of a seed culture medium was sterilized and *Arthrobacter globiformis* IFO 12137 was inoculated and shake cultured at 26° C. for 24 hours. One and a half ml of the seed culture prepared as described above was inoculated into an Erlenmeyer flask containing 30 ml of a growth medium. The inoculated flask was shake cultured at 26° C., 220 r.p.m., for 24 hour. Cells were collected from 120 ml of the cultured broth by centrifugation and after washing 2 times with 50 mM phosphate buffer (pH 7.0), resuspended into 20 ml of 100 mM phosphate buffer (pH 7.0) containing 1.0% maleic acid, and 0.1% NaCl. The reaction mixture thus prepared was incubated in a large test tube with shaking (195 r.p.m.) at 26° C.

The composition of the seed medium was: glucose 1%, peptone 0.5%, meat extract 0.3%, yeast extract 0.3%, NaCl 0.25%, pH 7.0. The composition of the growth medium was: glucose 1%, $NH_4Cl$ 0.1%, $KH_2PO_4$ 0.14%, $Na_2HPO_4.12H_2O$ 0.31%, MgSO 0.025%, meat extract 0.5%, citraconic acid as indicated in Table 2, pH 7.0.

After incubation of the reaction mixture for 19.5 to 48 hours, malic acid was produced and its optical purity (expressed as enantiomer excess, e.e.%) was determined. As shown in Table 2, after 48 hour incubation 4.7 g/liter of (R)-malic acid (e.e.73%) was produced even with the cells grown in a medium containing no citraconic acid. The cells grown in a medium containing citraconic acid produced (R)-malic acid more rapidly.

TABLE 2

| | Malic acid production (g/liter) and optical purity (e.e. %) of the produced (R)-malic acid | | | |
|---|---|---|---|---|
| Incubation Time | Citraconic Acid Added into Growth Medium | | | |
| (hours) | 0% | 0.5% | 1.0% | 2.0% |
| 19.5 | 0.3 g/l | 5.2 g/l (73)* | 5.2 g/l (71) | 5.0 g/l (81) |
| 24.0 | 0.3 g/l | 7.2 g/l (80) | 6.4 g/l (79) | 3.9 g/l (78) |
| 28.0 | 0.4 g/l | 4.6 g/l (79) | 6.2 g/l (81) | 3.2 g/l (61) |
| 48.0 | 4.7 g/l (73) | 0.5 g/l | 0.2 g/l | 3.0 g/l (58) |

*The values in parentheses are e.e. %.

EXAMPLE 2

The same procedures as in Examples 1 were repeated except that *Pseudomonas fragi* IFO 3458, *Pseudomonas putida* IFO 3738 and *Arthrobacter oxydans* IFO 12138 were used as the microorganism. (R)-malic acid was produced as shown in Table 3. The result shown in Table 3 also shows the effect of citraconic acid in the growth medium.

TABLE 3

| | Malic acid production (g/liter) and optical purity (e.e. %) of the produced (R)-malic acid | | | | |
|---|---|---|---|---|---|
| | Strain | | | | |
| | IFO 3458 | | IFO 3738 | | IFO 12138 |
| Incubation Time | Citraconic Acid Added (g/liter) | | | | |
| (hours) | 0 | 10 | 0 | 10 | 0 |
| 19.5 | 0.2 g/l | 2.3 g/l (100)* | 0.2 g/l | 0.7 g/l | 0.2 g/l |
| 28 | 0.3 g/l | 3.4 g/l (88) | 0.3 g/l | 0.3 g/l | 2.2 g/l (57) |

TABLE 3-continued

| | Malic acid production (g/liter) and optical purity (e.e. %) of the produced (R)-malic acid | | | | |
|---|---|---|---|---|---|
| | Strain | | | | |
| | IFO 3458 | | IFO 3738 | | IFO 12138 |
| Incubation Time (hours) | Citraconic Acid Added (g/liter) | | | | |
| | 0 | 10 | 0 | 10 | 0 |
| 48 | 0.3 g/l | 0.9 g/l | 0.2 g/l | 0.2 g/l | 0.4 g/l |

*The values in parentheses are e.e. %.

EXAMPLE 3

The same procedures as in Example 1 were repeated except that *Brevibacterium helvolum* ATCC 11822 was used as the microorganism and a medium supplemented with 1% citraconic acid was used as the growth medium. In this case, 4.4 g/liter of (R)-malic acid was produced after 48 hours incubation and the optical purity (e.e.) of the (R)-malic acid was 100%. After centrifugation of the reaction mixture, the clear supernatant was passed through a column of strongly acidic cation exchange resin (Dowex 50, H+ form) and then loaded on a column of strongly basic anion exchange resin (Dowex-1X8, formate form). The column was washed with water and then the acids were eluted stepwise with increasing strength of aqueous formic acid. Fractions of the effluent containing malic acid (eluted between 0.5 N and 1 N formic acid) was collected and concentrated to syrup. The syrup was cooled and crystals appeared was washed with small amount of cold acetonitrile and dried. The yield of the (R)-malic acid isolated was 2.5 g from 1 liter of the reaction mixture and its optical purity (e.e.) was 100%.

EXAMPLE 4

The same procedures as in Example 3 were repeated except that the microorganisms as shown in Table 4 were used. The concentration of the malic acid produced and the optical purity (e.e.) of the (R)-malic acid produced were shown in Table 4.

TABLE 4

| | Malic Acid Produced (g/liter) | | Optical Purity [(R)-Malic acid, e.e. %] | |
|---|---|---|---|---|
| Microorganism | 24 Hours | 48 Hours | 24 Hours | 48 Hours |
| *Pseudomonas fluorescence* IFO 3081 | | 2.8 | | 89 |
| *Pseudomonas pseudoalcaligenes* ATCC 12815 | 3.2 | 4.8 | 83 | 81 |
| *Corynebacterium acetoacidophilum* ATCC 13870 | | 2.3 | | 93 |
| *Corynebacterium callunae* ATCC 15991 | | 2.7 | | 90 |
| *Corynebacterium glutamicum* ATCC 31808 | | 2.0 | | 83 |
| *Corynebacterium vitarumen* ATCC 10234 | 5.9 | | 85 | |
| *Arthrobacter nicotianae* ATCC 21279 | 1.6 | | 52 | |
| *Arthrobacter citreus* AICC 17775 | 1.2 | | 100 | |
| *Arthrobacter ureafaciens* ATCC 7562 | 3.2 | | 85 | |
| *Bacillus alvei* ATCC 6344 | 2.7 | | 88 | |
| *Bacillus brevis* ATCC 8185 | 5.7 | | 88 | |
| *Acinetobacter calcoaceticus* ATCC 14987 | 4.6 | | 81 | |

EXAMPLE 5

The same procedures as in Example 1 were repeated except that *Arthrobacter globiformis* IFO 12137 was used as microorganism and growth medium was supplemented with 0.5% citraconic acid and the reaction mixture was incubated statically. After reaction for 24 hours, 6.3 g/liter of (R)-malic acid (e.e. 99%) was produced, and after 48 hour reaction, 9.1 g/liter of (R)-malic acid (e.e. 91%) was produced.

EXAMPLE 6

Cell-free extract was prepared by sonic treatment of the cells of the microorganisms used in Example 3 and Example 4. Except that the cell-free extract as above prepared was used in place of the cells in reaction mixture, the same procedures as in Example 3 and Example 4 were repeated. About 1.0 g/liter of (R)-malic acid was produced with each microorganism.

EXAMPLE 7

*Brevibacterium helvolum* ATCC 11822 was shake cultured in a 300 ml Erlenmeyer flask containing 30 ml of a sterilized medium consisting of 3% glucose, 0.5% $K_2HPO_4$, 0.5% $KH_2PO_4$, 0.025% $MgSO_4.7H_2O$, 0.001% $FeSO_4.4H_2O$, 0.001% $MnSO_4.4H_2O$, 0.5% meat extract, 0.3% yeast extract, 0.5% peptone, 0.5% citraconic acid (pH 7.0) at 26° C. for 24 hours. Cells were collected from the culture by centrifugation and suspended into 30 ml of 4% maleic acid solution (pH of the solution was adjusted to 7.0 with NaOH). The reaction mixture thus prepared was incubated statically at 35° C. for 72 hours. (R)-malic acid was produced at a concentration of 4.44% in the reaction mixture and the optical purity (e.e.) of the (R)-malic acid was 98.0%.

EXAMPLE 8

*Brevibacterium helvolum* ATCC 11822 was shake cultured in a 300 ml Erlenmeyer flask containing 3u ml of a sterilized medium consisting of 2% glucose, 0.5% $NH_4Cl$, 0.5% $K_2HPO_4$, 0.5% $KH_2PO_4$, 0.025% $MgSO_4.7H_2O$, 0.001% $FeSO_4.7H_2O$, 0.001% $MnSO_4.4H_2O$, 0.5% meat extract, 0.3% yeast extract, 0.5% peptone and the balance water (pH 7.0) at 26° C. for 24 hours. Cells were collected by centrifugation and treated with cold acetone. Thus prepared acetone-dried cells were suspended in 4% maleic acid solution (pH 7.0 with NaOH) to produce 30 ml of reaction mixture. The reaction mixture was incubated statically at 35° C. for 72 hours. (R)-malic acid was produced at a concentration of 3.03% in the reaction mixture and the optical purity (e.e.) of the (R)-malic acid was 87.1%.

EXAMPLE 9

*Brevibacterium ketoglutamicum* ATCC 15587 was shake cultured in a 300 ml Erlenmeyer flask containing 30 ml of a sterilized medium consisting of 1% glucose, 0.1% $NH_4Cl$, 0.14% $KH_2PO_4$, 0.3% $Na_2HPO_4.12H_2O$, 0.025% $MgSO_4.7H_2O$, 0.5% meat extract, 1% citraconic acid and the balance water (pH 7.0) at 26° C. for 24 hours. Cells were collected by centrifugation and suspended into 5 ml of 100 mM phosphate buffer (pH 7.0) containing 1% maleic acid in a large test tube and shake cultured at 26° C. for 48 hours. (R)-malic acid was produced at a concentration of 1.09 g/liter in the reaction mixture and the optical purity (e.e.) of the (R)-malic acid was 85%.

EXAMPLE 10

The same procedures as in Example 5 were repeated except that *Arthrobacter globiformis* IFO 12137 was used as the microorganism. After 20 hour reaction, (R)-malic acid was produced at a concentration of 4.3 g/liter and the optical purity (e.e.) of the (R)-malic acid was 79.8%. The reaction mixture was centrifuged to obtain supernatant. The supernatant (255 ml) was adjusted to pH 4.5 and boiled 10 minutes at 100° C. After the boiling, the formed precipitate was removed and the clear supernatant obtained was passed through a column of strongly acidic cation exchange resin (Diaion SK-1B, 20 to 50 mesh, $H^+$ form) 50 ml and then loaded on a column of strongly basic anion exchange resin (Dowex 1X8, 50 to 100 mesh, formate form) 50 ml. The latter column was washed twice with 100 ml distilled water and the malic acid was eluted with 1 N formic acid. The fraction containing malic acid was collected and concentrated in vaccuo to syrup. The crystal appeared after cooling the syrup was washed with small amount of cold acetonitrile and dried to obtain 0.276 g (R)-malic acid. The chemical purity and optical purity (e.e.( of the crystal was 92.2% and 98.5%, respectively. Mother liquor of the crystal and the acetonitrile-washed crystal solution were mixed and concentrated under reduced pressure, and 0.266 g of (R)-malic acid was obtained by repeating crystallization and washing. The chemical purity and optical purity of the second crystal were 89.3% and 100%, respectively.

EXAMPLE 11

Cells of *Brevibacterium helvolum* ATCC 11822 grown on a medium containing 2% citraconic acid, 5% meat extract, 0.1% $NH_4Cl$, 0.14% KH, 0.31% $Na_2HPO_4.12-H_2O$, 0.025% $MgSO_4.7H_2O$ (pH 7.0) was disrupted by sonication. Proteins precipitated with ammonium sulfate (43 to 60% saturation) was further purified by chromatography on Sepharose 4B gel. Thus, the activity of the maleate hydratase increased 16-fold compared with that of cell-free extract by the procedures described above.

EXAMPLE 12

Microorganisms shown in Table 5 were shake cultured in a 300 ml Erlenmeyer flask which contains a sterilized medium consisting of 1% glucose, 0.5% $NH_4Cl$, 0.5% $K_2HPO_4$, 0.5% $KH_2PO_4$, 0.025% $MgSO_4.7H_2O$, 0.001% $MnSO_4.4H_2O$, 0.5% meat extract, 0.5% peptone, 0.3% yeast extract, 0.5% citraconic acid and the balance water (pH 7.0) at 26° C., 220 r.p.m. for 24 hours. Cells were collected from the culture by centrifugation and after 2-times washing with 50 mM phosphate buffer (pH 7.0) suspended into 5 ml of 50 mM phosphate buffer (pH 7.0) containing 1% maleic acid and 0.1% NaCl. The reaction mixture thus prepared was incubated statically at 26° C. for 72 hours. Malic acid concentration in the reaction mixture at 24 hour incubation, 48 hour incubation and 72 hour incubation were shown in Table 5. Optical purity of the malic acid produced as the percentage of (R)-malic acid was also shown in Table 5.

TABLE 5

| Microorganism | Malic Acid Produced and Optical Purity [% of (R)-form] | | |
|---|---|---|---|
| | 24 Hours | 48 Hours | 72 Hours |
| *Aeromonas punctata* | 2.2 g/l | 7.0 g/l | 8.2 g/l |
| ATCC 11163 | | (>95%) | (>95%) |
| *Aeromonas sp.* | 3.7 g/l | 8.7 g/l | 3.2 g/l |
| ATCC 21763 | (>95%) | (>95%) | (>95%) |
| *Alcaligenes faecalis* | 7.4 g/l | 7.6 g/l | 8.5 g/l |
| IFO 3160 | (>95%) | (>95%) | (>95%) |
| *Escherichia coli* | 2.1 g/l | 5.7 g/l | 8.9 g/l |
| ATCC 4157 | | (>95%) | (>95%) |
| *Escherichia coli* | 1.7 g/l | 6.1 g/l | 9.3 g/l |
| ATCC 10798 | | (>95%) | (>95%) |
| *Microbacterium ammoniaphilum* | 4.4 g/l | 4.6 g/l | 6.5 g/l |
| ATCC 15354 | | | (>95%) |
| *Proteus mirabilis* | 4.9 g/l | 7.9 g/l | 8.7 g/l |
| ATCC 15290 | | (>95%) | (>95%) |
| *Providencia stuarti* | 3.7 g/l | 7.8 g/l | 9.1 g/l |
| ATCC 25825 | | (>95%) | (>95%) |

EXAMPLE 13

Microorganisms shown in Table 6 were shake cultured in a 300 ml Erlenmeyer flask which contains a sterilized medium at 26° C., 220 r.p.m. for 24 hours (bacteria) or 48 hours (yeast and fungi). Cells were collected from the culture by centrifugation and after 2-times washing with 50 mM phosphate buffer (pH 7.0) suspended into 5 ml of 50 mM phosphate buffer (ph 7.0) containing 1% maleic acid and 0.1% NaCl. The reaction mixture thus prepared was incubated statically at 26° C. for 96 hours.

The composition of the medium for bacteria consisted of 1% glucose, 0.5% $NH_4Cl$, 0.5% $K_2HPO_4$, 0.5% $KH_2PO_4$, 0.025% $MgSO_4.7H_2O$, 0.001% $MnSO_4.4H_2O$, 0.5% meat extract, 0.5% citraconic acid and the balance water (pH 7.0). For the growth of yeast, yeast extract (0.2%) was supplemented to the above-described medium for bacteria and the concentration of meat extract in the medium was changed to 0.3%. The pH of the medium for yeast was adjusted to 6.0. For the growth of fungi, yeast extract (0.2%) and meat extract (0.2%) were supplemented to the medium for bacteria and the concentration of meat extract in the medium was changed to 0.1%. The pH of the medium for fungi was adjusted to pH 5.5.

Malic acid concentration in the reaction mixture at 24 hour incubation, 48 hour incubation and 96 hour incubation were shown in Table 6. Optical purity of the malic acid produced as the percentage of (R)-malic acid was also shown in Table 6.

TABLE 6

| Microorganism | Malic Acid Produced and Optical Purity [% of (R)-form] | | |
|---|---|---|---|
| | 24 Hours | 48 Hours | 96 Hours |
| *Paracoccus denitrificans* ATCC 19367 | 6.0 g/l | 9.4 g/l | 8.7 g/l (99.9%) |
| *Protaminobacter ruber* IFO 3708 | 0.5 g/l | 0.8 g/l | 1.4 g/l (99.9%) |
| *Serratia rubidae* ATCC 11634 | 2.3 g/l | 6.0 g/l | 7.0 g/l (99.8%) |
| *Xanthomonas translucens* IFO 13558 | 6.0 g/l | 9.5 g/l | 7.7 g/l (99.9%) |
| *Amycoplatopsis orientalis* ATCC 19795 | 6.2 g/l | 7.1 g/l | 7.2 g/l -(99.9%) |
| *Streptomyces coelicolor* ATCC 10147 | 4.3 g/l | 9.6 g/l | 10.4 g/l (99.9%) |
| *Rhodococcus erythropolis* IFO 12320 | 4.4 g/l | 6.5 g/l | 9.4 g/l (99.9%) |
| *Cellulomonas cellasea* ATCC 487 | 4.7 g/l | 7.7 g/l | 10.3 g/l (99.9%) |
| *Hafnia alvei* ATCC 9760 | 3.8 g/l | 9.4 g/l | 7.6 g/l |

TABLE 6-continued

| Microorganism | Malic Acid Produced and Optical Purity [% of (R)-form] | | |
|---|---|---|---|
| | 24 Hours | 48 Hours | 96 Hours |
| Cytophaga sp. ATCC 9760 | 0.4 g/l | 0.6 g/l | 1.3 g/l (99.9%) |
| Flavobacterium aquatile ATCC 8375 | 2.3 g/l | 4.0 g/l | 5.7 g/l (99.8%) |
| Klebsiella pneumoniae ATCC 8308 | 2.5 g/l | 4.1 g/l | 6.0 g/l (99.9%) |
| Micrococcus aurantiacus ATCC 11731 | 1.4 g/l | 2.5 g/l | 4.4 g/l (99.6%) |
| Ancylobacter sp. ATCC 21373 | 1.7 g/l | 3.8 g/l | 6.2 g/l (99.6%) |
| Morganella morganii ATCC 25830 | 0.3 g/l | 0.6 g/l | 1.3 g/l (99.9%) |
| Planococcus citreus ATCC 14404 | 0.7 g/l | 1.2 g/l | 1.6 g/l (99.9%) |
| Kluyvera cryocrescens ATCC 14238 | 2.1 g/l | 4.9 g/l | 7.8 g/l (100.0%) |
| Kurthia zopfii ATCC 10538 | 0.3 g/l | 0.5 g/l | 1.3 g/l (99.9%) |
| Achromobacter cycloclastes ATCC 21921 | | | 10.4 g/l (99.9%) |
| Citrobacter freundii ATCC 6750 | | | 6.6 g/l (99.8%) |
| Saccharomyces cerevisiae ATCC 18824 | | | 3.7 g/l (99.9%) |
| Saccharomycopsis lipolytica IFO 0746 | | | 0.88 g/l (98.6%) |
| Yarrowia lipolytica ATCC 16617 | | | 1.1 g/l (>99.9%) |
| Candida utilis ATCC 9950 | | | 0.43 g/l (81.8%) |
| Candida utilis IFO 1086 | | | 0.40 g/l (79.0%) |
| Debaryomyces polymorphus IFO 1189 | | | 0.71 g/l (95.5%) |
| Hansenula subpelliculosa IFO 0808 | | | 0.67 g/l (97.0%) |
| Kloeckera apiculata IFO 0175 | | | 1.95 g/l (98.6%) |
| Hansenula wickerhamii ATCC 16767 | | | 0.71 g/l (96.5%) |
| Kloeckera javanica IFO 1094 | | | 3.83 g/l (>99.9%) |
| Kluyveromyces wickerhamii IFO 1675 | | | 0.32 g/l (75.5%) |
| Lipomyces starkeyi ATCC 20147 | | | 0.87 g/l (96.0%) |
| Rhodotorula glutinis ATCC 20147 | | | 3.64 g/l (99.9%) |
| Schizosaccharomyces pombe ATCC 2476 | | | 0.68 g/l (93.4%) |
| Torulopsis pinus ATCC 22996 | | | 4.31 g/l (99.6%) |
| Torulopsis spherica ATCC 8549 | | | 0.26 g/l (80.3%) |
| Trichosporon cutaneum IFO 0173 | | | 0.54 g/l (87.3%) |
| Trigonopsis variabilis IFO 0755 | | | 0.52 g/l (93.4%) |
| Aspergillus niger ATCC 6275 | | | 8.11 g/l (99.9%) |
| Aspergillus oryzae var. viridis ATCC 22788 | | | 5.85 g/l (98.5%) |
| Penicillium chrysogenum ATCC 9480 | | | 5.98 g/l (99.1%) |
| Penicillium citrinum ATCC 14994 | | | 4.15 g/l (91.4%) |
| Rhizopus chinensis var. liquefaciens IFO 4737 | | | 1.96 g/l (96.7%) |
| Trichoderma reesei ATCC 13631 | | | 5.03 g/l (98.8%) |
| Trichoderma longibrachiatum IFO 4847 | | | 5.02 g/l (99.3%) |

While the invention has been described in detail and with reference to specific embodiments thereof, it will be apparent to one skilled in the art that various changes and modifications can be made therein without departing from the spirit and scope thereof.

What is claimed is:

1. A method for producing (R)-malic acid comprising hydrating maleic acid by contacting in a reaction medium, maleic acid with (A) a microbial maleate hydratase or (B) a microorganism containing said maleate hydratase, to form (R)-malic acid, wherein said microorganism is a microorganism belonging to one of the genera Arthrobacter, Brevibacterium, Cornebacterium, Bacillus, Acinetobacter, Microbacterium, Aeromonas, Escherichia, Alcligenes, Proteus, Providencia, Paracoccus, Protaminobacter, Serratia, Xanthomonas, Amycoplatopsis, Streptomyces, Rhodococcus, Cellulomonas, Hafnia, Cytophaga, Flavobacterium, Klebsiella, Micrococcus, Ancylobacter, Morganella, Planococcus, Kluyvera, Kurthia, Achromobacter, Citrobacter, Saccharomyces, Saccharomycopsis, Yarrowia, Candida, Debaryomyces, Hansenula, Kloeckera, Kluyveromyces, Lipomyces, Rhodotorula, Schizosaccharomyces, Torulopsis, Trichosporon, Trigonopsis, Aspergillus, Penicillium, Rhizopus, and Trichoderma.

2. The method claimed in claim 1, wherein said microorganism is a microorganism of the species selected from the group consisting of Arthrobacter citreus, Arthrobacter oxydans, Arthrobacter nicotianae, Arthrobacter ureafaciens, Arthrobacter globiformis, Brevibacterium helvolum, Brevibacterium ketoglutamicum, Corynebacterium acetoacidophilum, Corynebacterium callunae, Corynebacterium glutamicum, Corynebacterium vitarumen, Bacillus alvei, Bacillus brevis, Acinetobacter calcoaceticus, Aeromonas punctata, Alcaligenes faecalis, Escherichia coli, Microbacterium ammoniaphilum, Proteus mirabilis, Providencia stuarti, Paracoccus denitrificans, Protaminobacter ruber, Serratia rubidae, Xanthomonas translucens, Amycoplatopsis orientalis, Streptomyces coelicolor, Rhodococcus erythropolis, Cellulomonas cellasea, Hafnia alvei, Flavobacterium aquatile, Klebsiella pneumoniae, Micrococcus aurantiacus, Morganella morganii, Planococcus citreus, Kluyvera cryocrescens, Kurthia zopfii, Achromobacter cycloclastes, Citrobacter freundii, Saccharomyces cerevisiae, Saccharomycopsis lipolytica, Yarrowia lipolytica, Candida utilis, Debaryomyces polymorphus, Hansenula subpelliculosa, Kloeckera apiculata, Hansenula wickerhamii, Kloeckera javanica, Kluyveromyces wickerhamii, Lipomyces starkeyi, Rhodotorula glutinis, Schizosaccharomyces pombe, Torulopsis pinus, Torulopsis spherica, Trichosporon cutaneum, Trigonopsis variabilis, Aspergillus niger, Aspergillus oryzae var. viridis, Penicillium chrysogenum, Penicillium citrinum, Rhizopus chinensis var. liquefaciens, Trichoderma reesei, and Trichoderma longibrachiatum.

3. The method as claimed in claim 1, wherein said microorganism is a strain having taxonomic characteristics of a strain selected from the group consisting of Arthrobacter citreus ATCC 17775, Arthrobacter oxydans IFO 12138, Arthrobacter globiformis IFO 12137, Arthrobacter nicotianae ATCC 21279, Arthrobacter ureafaciens ATCC 7562, Brevibacterium helvolum ATCC 11822, Brevibacterium ketoglutamicum ATCC 15587, Corynebacterium acetoacidophilum ATCC 13870, Corynebacterium callunae ATCC 15991, Corynebacterium glutamicum ATCC 31808, Corynebacterium vitarumen ATCC 10234, Bacillus alvei ATCC 6344, Bacillus brevis ATCC 8185, Acinetobacter calcoaceticus ATCC 14987, Aeromonas punctata ATCC 11163, Aeromonas sp. ATCC 21763, Alcaligenes faecalis IFO 3160, Escherichia coli ATCC 4157, Escherichia coli ATCC 10798, Microbacterium

*ammoniaphilum* ATCC 15354, *Proteus mirabilis* ATCC 15290, *Providencia stuarti* ATCC 25825, *Paracoccus denitrificans* ATCC 19367, *Protaminobacter ruber* IFO 3708, *Serratia rubidae* ATCC 11634, *Xanthomonas translucens* IFO 13558, *Amycoplatopsis orientalis* ATCC 19795, *Streptomyces coelicolor* ATCC 10147, *Rhodococcus erythropolis* IFO 12320, *Cellulomonas cellasea* ATCC 487, *Hafnia alvei* ATCC 9760, *Cytophaga* sp. ATCC 9760, *Flavobacterium aquatile* ATCC 8375, *Klebsiella pneumoniae* ATCC 8308, *Micrococcus aurantiacus* ATCC 11731, *Ancylobacter* sp. ATCC 21373, *Morganella morganii* ATCC 25830, *Planococcus citreus* ATCC 14404, *Kluyvera cryocrescens* ATCC 14238, *Kurthia zopfii* ATCC 10538, *Achromobacter cycloclastes* ATCC 21921, *Citrobacter freundii* ATCC 6750, *Saccharomyces cerevisiae* ATCC 18824, *Saccharomycopsis lipolytica* IFO 0746, *Yarrowia lipolytica* ATCC 16617, *Candida utilis* IFO 1086, *Debaryomyces polymorphus* IFO 1189, *Hansenula subpelliculosa* IFO 0808, *Kloeckera apiculata* IFO 0175, *Hansenula wickerhamii* ATCC 16767, *Kloeckera javanica* IFO 1094, *Kluyveromyces wickerhamii* IFO 1675, *Lipomyces starkeyi* ATCC 2014, *Rhodotorula glutinis* ATCC 20147, *Schizosaccharomyces pombe* ATCC 2476, *Torulopsis pinus* ATCC 22996, *Torulopsis spherica* ATCC 8549, *Trichosporon cutaneum* IFO 0173, *Trigonopsis variabilis* IFO 0755, *Aspergillus niger* ATCC 6275, *Aspergillus oryzae* var. viridis ATCC 22788, *Penicillium chrysogenum* ATCC 9480, *Penicillium citrinum* ATCC 14994, *Rhizopus chinensis* var. liquefaciens IFO 4737, *Trichoderma reesei* ATCC 13631, and *Trichoderma longibrachiatum* IFO 4847.

4. The method as claimed in claim 1, wherein hydrating maleic acid to form (R)-malic acid is performed at 5° to 50° C., and at pH 4 to 10 for 1 to 100 hours, with the concentration of said maleic acid 0.05 to 30% based on the weight of the reaction medium.

5. The method as claimed in claim 1, wherein said maleic hydratase has the following characteristics:
(1) Action and specificity; said enzyme catalyzes a reaction in which maleic acid is hydrated to form (R)-malic acid, but does not act on fumaric acid,
(2) Optimum pH; said enzyme is active at pH 6.0 to 9.0,
(3) pH stability; said enzyme is stable at pH 6.0 to 9.0,
(4) Optimum temperature; said enzyme is active at 20° to 50° C.,
(5) Temperature stability; said enzyme is stable below 35° C., but is inactivated at 45° C. or more,
(6) Molecular weight; said molecular weight of said enzyme estimated by the gel filtration method using Sepharose 4B is about $13.5 \times 10^{4d}$, and the molecular weight estimated by the gel filtration method using Sephacryl S-200 is about $6 \times 10^{4d}$, and
(7) Inhibitors; at a concentration of 1 mM, said enzyme is completely inhibited by p-chloromercuribenzoic acid, while EDTA and phenylmethlsulfonylfluoride do not inhibit activity, iodoacetic acid inhibits activity by 12%, sodium metaperiodate inhibits activity by 17% and at a concentration of 10 mM, N-ethylmalemide inhibits activity by 33%.

* * * * *